United States Patent
McNeil-Watson

(10) Patent No.: US 8,634,076 B2
(45) Date of Patent: Jan. 21, 2014

(54) MULTI-SAMPLE SCATTERING MEASUREMENTS

(75) Inventor: Fraser McNeil-Watson, Malvern (GB)

(73) Assignee: Malvern Instruments, Ltd. (GB)

( * ) Notice: Subject to any disclaimer, the term of this patent is extended or adjusted under 35 U.S.C. 154(b) by 222 days.

(21) Appl. No.: 12/857,878

(22) Filed: Aug. 17, 2010

(65) Prior Publication Data

US 2011/0157586 A1 Jun. 30, 2011

Related U.S. Application Data

(60) Provisional application No. 61/274,482, filed on Aug. 17, 2009.

(51) Int. Cl.
*G01N 21/00* (2006.01)

(52) U.S. Cl.
USPC .......................................... 356/343

(58) Field of Classification Search
USPC .......................................... 356/343
See application file for complete search history.

(56) References Cited

U.S. PATENT DOCUMENTS 5,741,412 A * 4/1998 Dovichi et al. ............... 204/602
6,091,492 A * 7/2000 Strickland et al. ............ 356/336

* cited by examiner

*Primary Examiner* — Tu Nguyen
(74) *Attorney, Agent, or Firm* — Kristofer E. Elbing

(57) ABSTRACT

In one general aspect, a multi-sample liquid scattering measurement apparatus is disclosed. It includes a coherent light source having an optical output axis, with sample cells that each include a volume that intersects with the optical output axis. Detectors are each positioned to detect scattered light resulting from an interaction between light from the coherent light source and one of the cells. Light scattering analysis logic is responsive to the detectors and operative to determine a property of a liquid sample in each of the sample cells based on the detected scattered light.

20 Claims, 4 Drawing Sheets

MULTI-SAMPLE SCATTERING MEASUREMENTS

CROSS-REFERENCE TO RELATED APPLICATION

This application claims the benefit of U.S. Provisional Application No. 61/274,482, filed Aug. 17, 2009, which is herein incorporated by reference.

FIELD OF THE INVENTION

This invention relates to methods and apparatus for measuring parameters of multiple fluid samples.

BACKGROUND OF THE INVENTION

Several approaches to measuring the properties of a number of fluids have been proposed, including methods that involve shining laser light vertically through cells in multi-well plates.

SUMMARY

In one general aspect, the invention features a multi-sample liquid scattering measurement apparatus that includes a coherent light source having an optical output axis. Sample cells each include a volume that intersects with the optical output axis, and detectors are each positioned to detect scattered light resulting from an interaction between light from the coherent light source and one of the cells. Light scattering analysis logic is responsive to the detectors and operative to determine a property of a liquid sample in each of the sample cells based on the detected scattered light.

In preferred embodiments the sample cells can be part of a linear array of sample cells. The linear array can be part of a larger two-dimensional array. The sample cells can be part of a unitary block. The coherent light source can be positioned to provide an optical axis that is at least generally horizontal, with the detectors each being positioned to receive light in a generally horizontal direction from one side of its corresponding sample cell. The coherent light source can be positioned to provide an optical axis that is at least generally horizontal, with the detectors being positioned to receive light in a generally horizontal direction from alternating sides of corresponding sample cells. The coherent light source can be positioned to provide an optical axis that is at least generally horizontal, with the detectors being positioned to receive light in a generally vertical direction from bottom surfaces of corresponding sample cells. The coherent light source can be positioned to provide an optical axis that is at least generally horizontal, with the detectors being positioned to receive light in a generally vertical direction from tops of corresponding sample cells. The coherent light source can be a laser. The coherent light source can be an unfocussed laser. The apparatus can further include an environmental control system proximate the plurality of cells for regulating the temperature of the cells. The apparatus can further include one or more lenses disposed between the sample cells in the plurality of sample cells. The detectors can be photon counting detectors, with the light scattering analysis logic being dynamic light scattering analysis logic. The light scattering analysis logic can be static light scattering analysis logic. At least part of the sample cells can be disposable. The apparatus can further include parallel loading fluid handling equipment operative to simultaneously load the liquid samples into the sample cells. This parallel loading fluid handling equipment can be operative to simultaneously transfer a plurality of liquid samples from a multi-well plate to the plurality of sample cells.

In another general aspect, the invention features a multi-sample liquid scattering measurement method that includes shining a beam of coherent light simultaneously through a plurality of liquid samples, detecting light scattered from each of the liquid samples, and deriving properties of the liquid samples based on the detected light. In preferred embodiments the method can further include the step of simultaneously transferring the liquid samples from a multi-well plate to the plurality of a sample cells before the step of shining a beam.

In a further general aspect, the invention features a multi-sample liquid scattering measurement apparatus, including means for shining a beam of coherent light simultaneously through a plurality of liquid samples, means for detecting light scattered from each of the liquid samples, and means for deriving properties of the liquid samples based on the detected light.

DETAILED DESCRIPTION OF AN ILLUSTRATIVE EMBODIMENT

Figure 1:
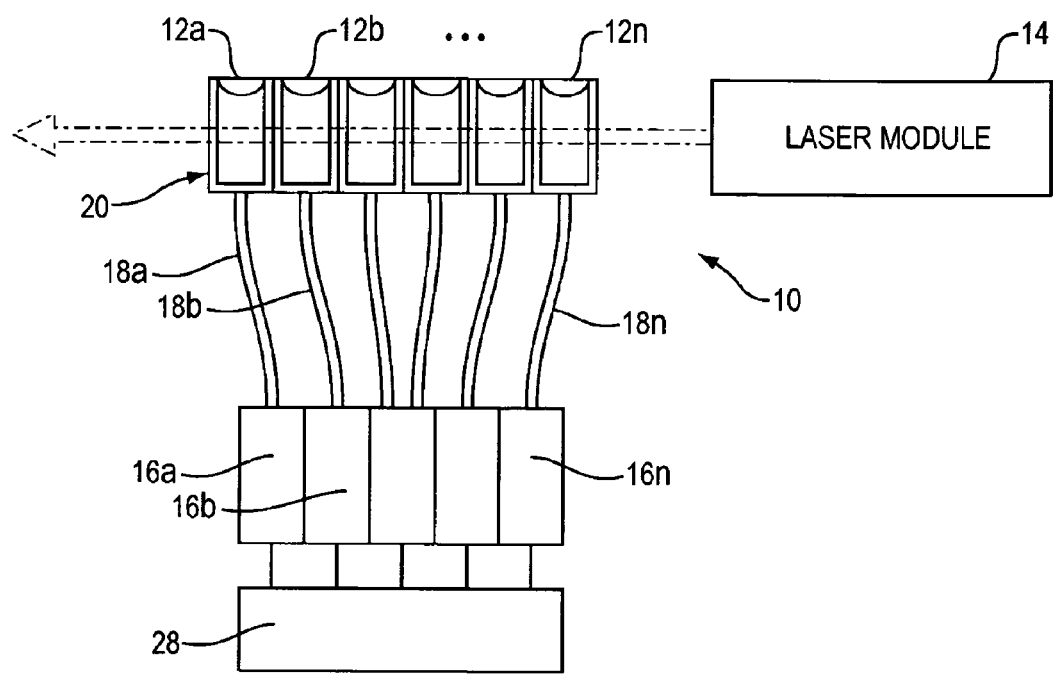
FIG. 1 is a diagrammatic side view of an illustrative multi-cell measurement instrument according to the invention.

Referring to FIG. 1, an illustrative multi-cell measurement instrument according to the invention includes a plurality of cells 12A, 12B . . . 12N, such as cuvettes, through which an illumination source 14, such as a laser, shines a beam of preferably coherent light. The cells are preferably arranged in a linear array, but it may also be possible to vary this arrangement, such as by staggering the cells, or using mirrors. A detector is associated with each of the cells, and these can be coupled to the cells via single- or multi-mode fibers, which can be each be equipped with a lens. The detectors can be photon-counting detectors, such as Avalanche Photo Diodes (APDs) or Photo Multiplier Tubes (PMTS). An attenuator can also be provided to attenuate the source.

Figure 2:
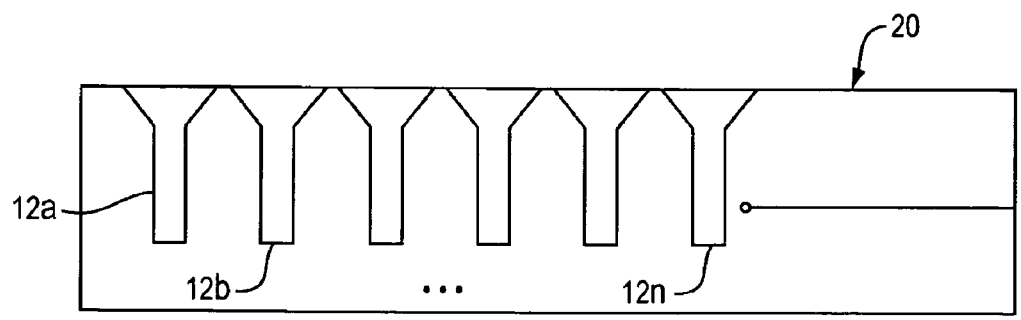
FIG. 2 is a diagrammatic side view of a sample cell array for use with an instrument such as the one shown in FIG. 1.

Referring also to FIG. 2, the linear array can be implemented as a six-wall glass or polymer array to minimize scattering interfaces. Samples can be transferred to the linear array in a variety of ways, such as using automated fluid handling equipment (e.g., pipettes or multi-pipette heads). In one embodiment, samples are transferred from standard multi-well plates (96/384/1536) on a line-by-line basis.

Figure 3:
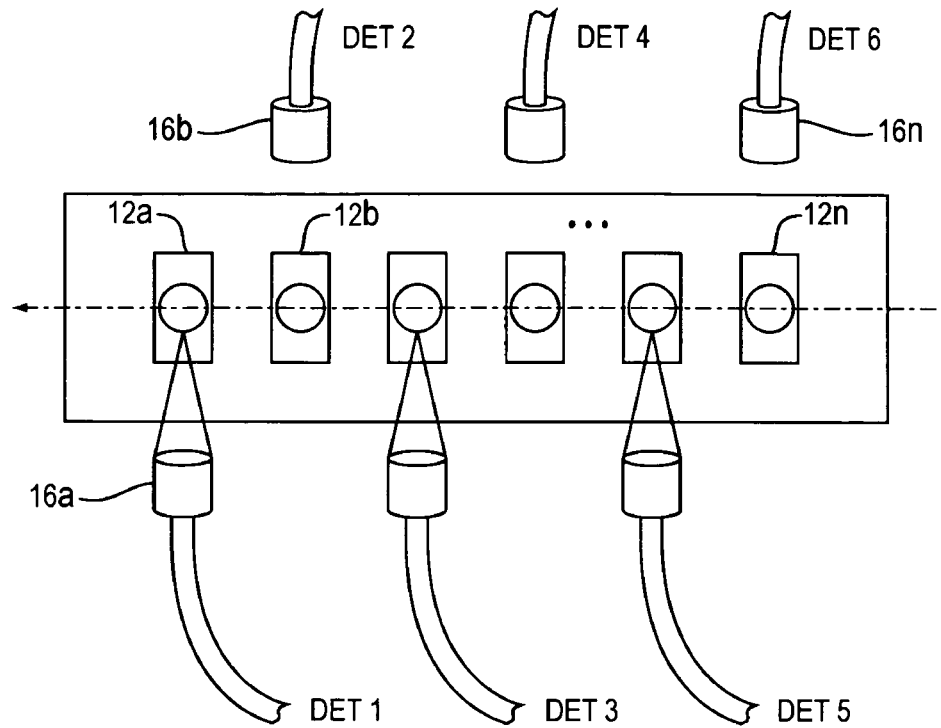
FIG. 3 is a diagrammatic perspective view of a sample cell array showing alternating detectors and an environmental control system.

Referring also to FIG. 3, detectors 16 can be located in any suitable location where they may detect scattered light. They can be on one side of the cells 12, for example, they can also be staggered on different sides of the cells, or they can be above or below the cells.

Figure 4:
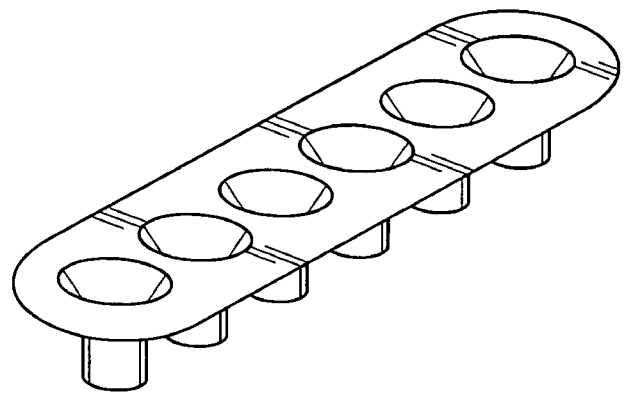
FIG. 4 is a diagrammatic perspective view of a sample cell array for use with interleaved minors.
Figure 5:
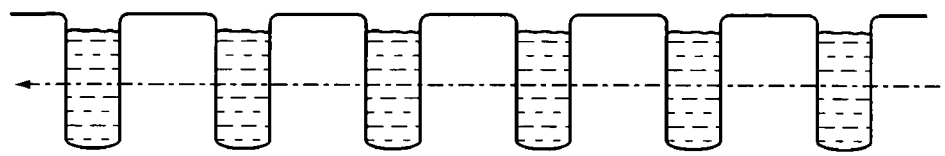
FIG. 5 is a diagrammatic cross-section of the sample cell array of FIG. 4.
Figure 6:
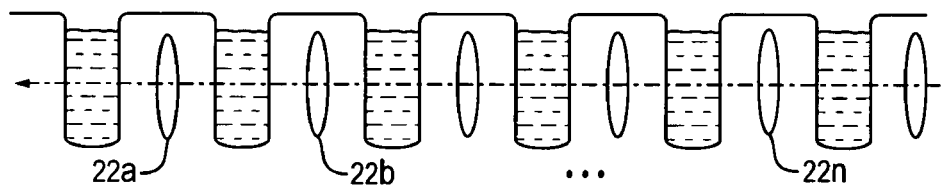
FIG. 6 is a diagrammatic cross section of the cell array of FIG. 4 shown in position with its interleaved minors.

Referring to FIGS. 4-6, a linear array can be implemented with gaps for lenses 22 allowing the laser beam to be focused in each cell.

Figure 7:
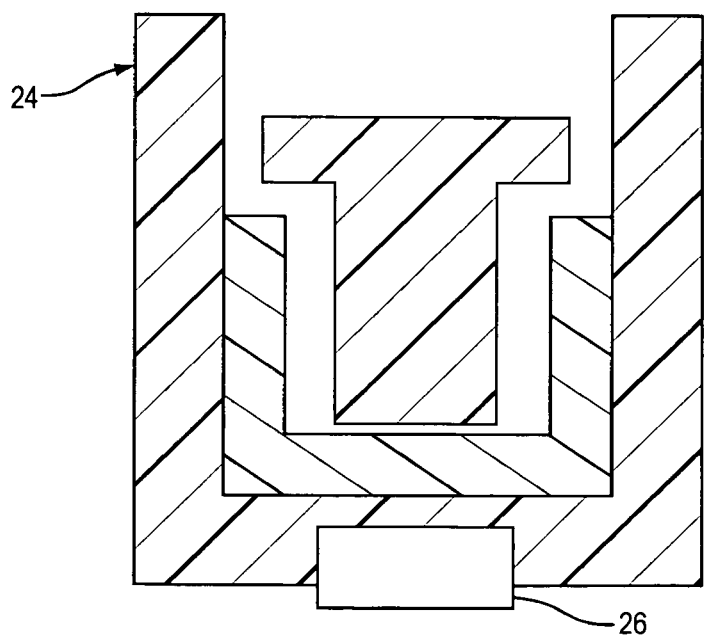
FIG. 7 is a diagrammatic end view of the cell array of FIG. 4 shown in position with its environmental control system.
Figure 8:
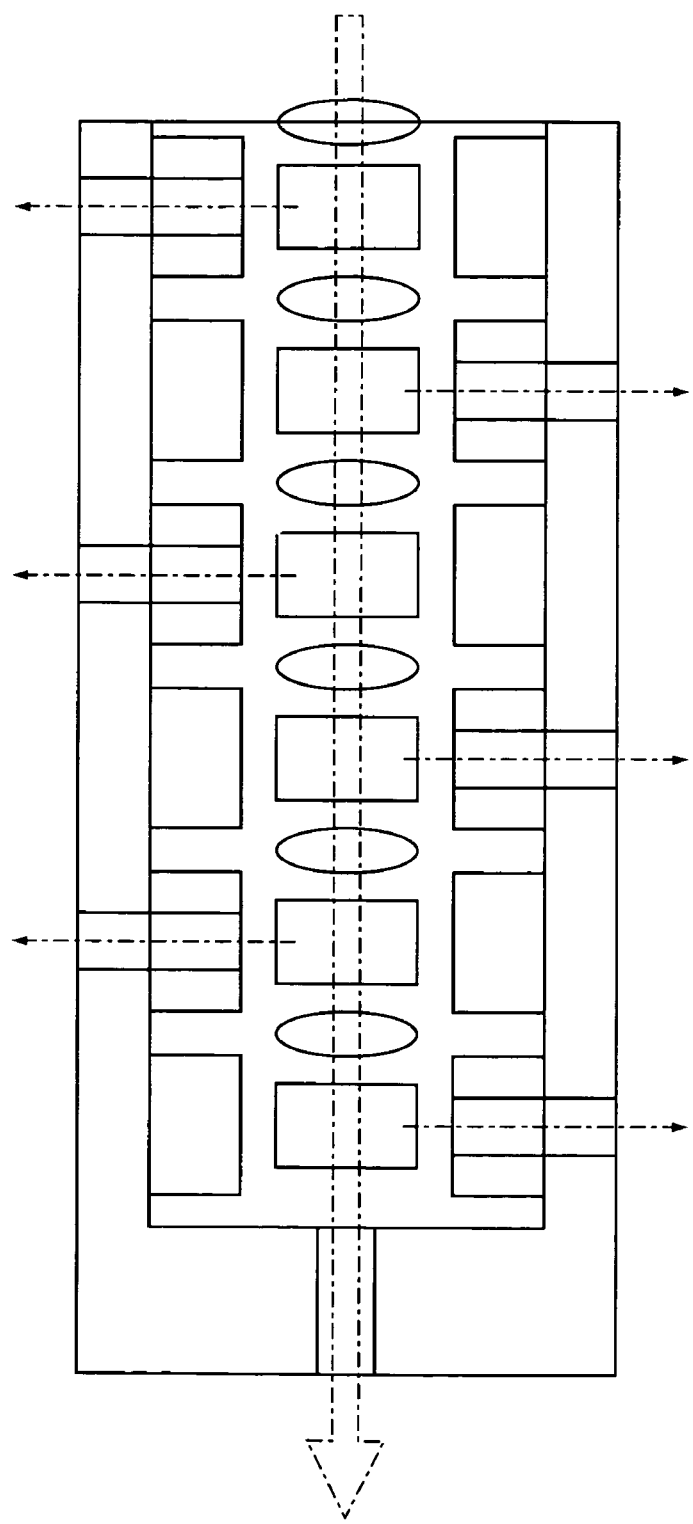
FIG. 8 is a diagrammatic top view of the cell array of FIG. 4 shown in position with its interleaved minors and environmental control system.

Referring to FIG. 7, the cells are preferably held in an environmentally controlled environment. For example, they can be held in an insulating jacket 24 above a Joule-Pelletier unit 26. This provides a thermally controlled enclosure at a stable known temperature, such as between 0 and 120 degrees C., normally around 25-35 degrees C.

Referring to FIG. 1, the detectors can provide or outputs to one or more scattering analysis processors 28 that can perform scattering analysis using a variety of well-known techniques, such as Dynamic Light Scattering (DLS) and Static Light Scattering (SLS). In the case of DLS, for example, the scattering analysis processor can include photon counting and correlation logic. These can be embodied in special-purpose software running on a general-purpose hardware, special-purpose hardware, or both.

In the simplest case an un-focused laser beam can pass through all the samples, which would be sufficiently dilute that attenuation of the beam was minimal. Individual fiber optics or bulk optics can relay scattered light from each cell cavity to separate detectors each connected to a separate signal processor to compute the size or diffusion coefficient of the material in each cavity using standard photon correlation spectroscopy, or to simply record the intensity of scattered light for an SLS measurement. Scattering angles of nominally 90 degrees or relatively close to it would generally be used.

In a more complex realization, lenses are inserted between each cavity to (re)focus the beam into each successive cavity. The cavities can be filled either individually manually or automatically in parallel using a pipetter array or by drawing samples from a multiwell plate (96/384/1536) in parallel using a set of ganged together syringes or some other pumping method. Each cuvette may also be illuminated via a separate fibee optic, in series or parallel.

Applications of the instrument can include a variety of types of fluids, such as measurements of dispersions of colloids, nano particles, polymers, biomolecules, and combinations of these.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

What is claimed is:

1. A multi-sample liquid scattering measurement apparatus, including:
   a coherent light source having an optical output axis,
   a plurality of walls that define a plurality of sample cells that each include a sample volume to hold one of the samples in place and wherein the optical output axis of the coherent light source passes through at least some of the walls to intersect with the sample volumes,
   a plurality of detectors each positioned to detect scattered light resulting from an interaction between light from the coherent light source and a sample held in the sample volume in one of the plurality of cells, and
   light scattering analysis logic responsive to the detectors and operative to determine a property of a liquid sample in each of the sample cells based on amounts of the detected scattered light detected by the detectors.

2. The apparatus of claim 1 wherein the sample cells are part of a linear array of sample cells.

3. The apparatus of claim 2 wherein the linear array is part of a larger two-dimensional array.

4. The apparatus of claim 1 wherein the sample cells are part of a unitary block.

5. The apparatus of claim 1 wherein the coherent light source is positioned to provide an optical axis that is at least generally horizontal and wherein the detectors in the plurality of detectors are each positioned to receive light in a generally horizontal direction from one side of its corresponding sample cell.

6. The apparatus of claim 1 wherein the coherent light source is positioned to provide an optical axis that is at least generally horizontal and wherein the detectors in the plurality of detectors are positioned to receive light in a generally horizontal direction from alternating sides of corresponding sample cells.

7. The apparatus of claim 1 wherein the coherent light source is positioned to provide an optical axis that is at least generally horizontal and wherein the detectors in the plurality of detectors are positioned to receive light in a generally vertical direction from bottom surfaces of corresponding sample cells.

8. The apparatus of claim 1 wherein the coherent light source is positioned to provide an optical axis that is at least generally horizontal and wherein the detectors in the plurality of detectors are positioned to receive light in a generally vertical direction from tops of corresponding sample cells.

9. The apparatus of claim 1 wherein the coherent light source is a laser.

10. The apparatus of claim 1 wherein the coherent light source is an unfocussed laser.

11. The apparatus of claim 1 further including an environmental control system proximate the plurality of cells for regulating the temperature of the plurality of cells.

12. The apparatus of claim 1 further including one or more lenses disposed between the sample cells in the plurality of sample cells.

13. The apparatus of claim 1 wherein the detectors are photon counting detectors and wherein the light scattering analysis logic is dynamic light scattering analysis logic.

14. The apparatus of claim 1 wherein the light scattering analysis logic is static light scattering analysis logic.

15. The apparatus of claim 1 wherein at least part of the sample cells is disposable.

16. The apparatus of claim 1 further including parallel loading fluid handling equipment operative to simultaneously load the liquid samples into the sample cells.

17. The apparatus of claim 16 wherein the parallel loading fluid handling equipment is operative to simultaneously transfer a plurality of liquid samples from a multi-well plate to the plurality of sample cells.

18. A multi-sample liquid scattering measurement method, comprising:
   shining a beam of coherent light along an optical axis that simultaneously passes through a plurality of liquid samples held in sample cells,
   detecting light scattered from each of the liquid samples, and deriving properties of the liquid samples based on amounts of the detected light.

19. The method of claim 18 further including the step of simultaneously transferring the liquid samples from a multi-well plate to the plurality of a sample cells before the step of shining a beam.

20. A multi-sample liquid scattering measurement apparatus, including:
   means for shining a beam of coherent light along an optical axis that simultaneously passes through a plurality of liquid samples held in sample cells,
   means for detecting light scattered from each of the liquid samples, and
   means for deriving properties of the liquid samples based on amounts of the detected light.

* * * * *